United States Patent [19]

McNeil

[11] Patent Number: 4,710,642
[45] Date of Patent: Dec. 1, 1987

[54] OPTICAL SCATTEROMETER HAVING IMPROVED SENSITIVITY AND BANDWIDTH

[76] Inventor: John R. McNeil, 13423 Desert Hills NE., Albuquerque, N. Mex. 87111

[21] Appl. No.: 767,611

[22] Filed: Aug. 20, 1985

[51] Int. Cl.[4] .............................................. G01N 21/86
[52] U.S. Cl. ..................................... 250/571; 356/445
[58] Field of Search ............... 250/562, 563, 571, 572; 356/445–448

[56] References Cited

U.S. PATENT DOCUMENTS 3,922,093 11/1975 Dandliker et al. ................... 250/571
4,364,663 12/1982 Gardner et al. ..................... 356/445
4,555,635 11/1985 Yoshida .............................. 250/572

Primary Examiner—David C. Nelms
Attorney, Agent, or Firm—William E. Hein

[57] ABSTRACT

An improved optical scatterometer includes a multiple detector array that enables the measurement of sample microstructure over an increased range of spatial frequency. One array of optical detectors is positioned in a plane perpendicular to the plane containing an incident laser beam and a specularly reflected beam to detect indications of back-scattered and forward-scattered light in that perpendicular plane. Two laser beams having different wavelengths may be employed to determine the optical characteristics of a film and an underlying substrate.

10 Claims, 5 Drawing Figures

OPTICAL SCATTEROMETER HAVING IMPROVED SENSITIVITY AND BANDWIDTH

BACKGROUND AND SUMMARY OF THE INVENTION

This invention relates generally to optical scatterometers and more specifically to an improved optical scatterometer exhibiting improved sensitivity and bandwidth characteristics. An optical scatterometer can be employed in a number of manufacturing environments that require knowledge of surface microstructure. Since the scatterometer technique is a noncontact diagnostic technique, it does not result in damage to the sample under investigation. In addition, the noncontact nature of the technique makes it more suited for production monitoring procedures. For example, for over a decade the optical scatterometer has been used to examine surfaces of optical components, such as dielectric mirrors, metal mirrors, and glass substrates. Similarly, finely machined components can be monitored with an optical scatterometer during manufacture. The present invention relates to an optical scatterometer useful for examining the microstructure of smooth optical components, magnetic and optical storage media, and semiconductor microelectronics components during fabrication. By monitoring the size distribution of microstructure of semiconductor silicon substrates and the film subsequently deposited on the substrates one can obtain quantitative information concerning component microstructure. This knowledge can then be employed in the manufacturing process to improve performance, yield, and lifetime of semiconductor products.

In operation of a scatterometer, the sample under examination is illumninated with light of visible or infrared wavelengths, and the light which is scattered by the sample is analyzed, as shown in the prior art scatterometer arrangement of FIG. 1. In the case of some samples, such as optical components, for example, knowledge of the scattered light is itself important. In the case of other samples, the fact that a surface scatters light might not be of direct importance. However, the scattered light can be analyzed to suggest characteristics of the microstructure of the sample under analysis. In the case of surfaces which do not transmit light at the wavelength of use in the scatterometer, the scattered light is indicative of the surface microstructure of the sample. Metallic surfaces are an example (e.g. Ag surface examined with light of wavelength 633 nm.) If the sample transmits light at the wavelength of use in the scatterometer, the scattered light is indicative of both surface and volume microstructure of the sample. An example of this situation is a thin film of $Si_3N_4$ on a silicon substrate being examined with light of wavelength 633 nm. The use of two light sources in one scatterometer includes both situations mentioned above, thus extending the current capabilities of the scatterometer analysis technique.

As used herein, the term microstructure refers to surface microroughness and the way in which the microroughness is distributed at different spatial frequencies, or differenect sizes, of structure on the surface of interest. This is to be distinguished from isolated surface defects and contaminants such as dust particles. However, the scatterometer described herein is useful for detecting and quantifying these on a surface as well.

There are two key requirements of an optical scatterometer. First, the scatterometer must be sufficiently sensitive to detect scatter from surfaces of the minimum microroughness of interest. Second, the scatterometer must be capable of detecting scatter from microstructure within the range of spatial frequencies, or sizes, of interest. For example, microelectronics processing requirements include minimizing the amount of microstructure as short as 0.5 micron ($\mu$) lateral dimension (2 inverse micron ($\mu^{-1}$) spatial frequency) on a surface. Hence, the scatterometer must be capable of detecting scattered light from structure of this size. The relation between microstructure size and scatterometer parameters is discussed below. These requirements are difficult to achieve, expecially when samples to be examined are very smooth, and therefore have low scatter. The present invention extends the capabilities of existing scatterometers in satisfying both requirements.

DETAILED DESCRIPTION OF THE INVENTION

Figure 1:
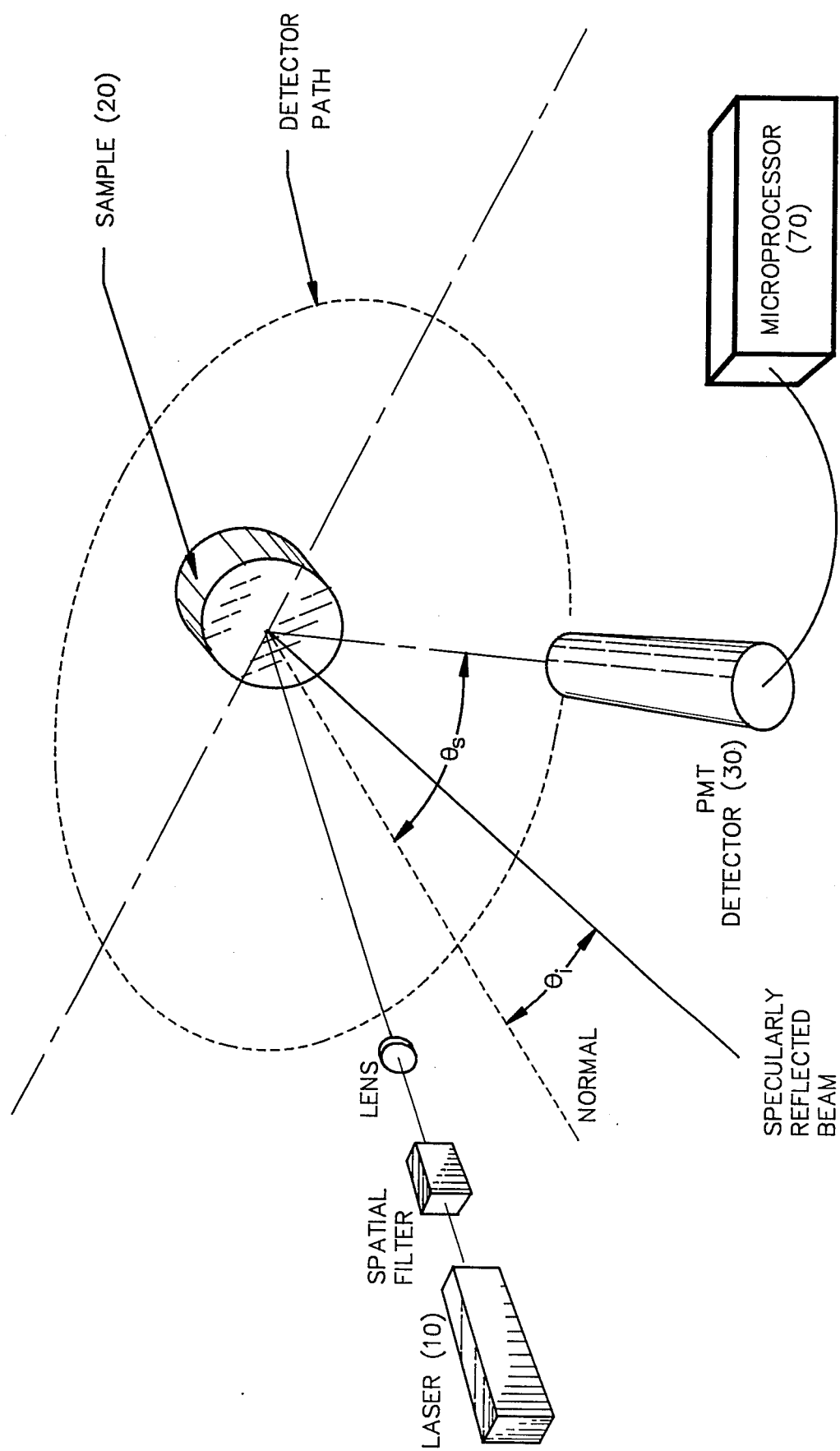
FIG. 1 is a diagram illustrating a single detector scatterometer constructed in accordance with the prior art.

Referring to FIG. 1, there is shown one common prior art arrangement currently employed for the optical scatterometer. The sample 20 under investigation is illuminated with a laser 10, and the light scattered by the sample is measured using the PMT detector 30 as illustrated. The scattered light is measured as a function of angle $\theta_s$, from the perpendicular to the surface. The scatter angle $\theta_s$ and the spatial frequency, f, of the structure responsible for the scattered light (i.e. the structure actually scattering light) are related by the equation $$f = 1/d = (\sin \theta_s - \sin \theta_i)/x$$

where d is the spatial wavelength (lateral dimension) of the microstructure, $\theta_i$ is the angle of incidence of the laser 10, and x is the wavelength of the laser light used in microns ($\mu$). This relation is applicable for light which is back-scattered from the sample (i.e. for $\theta_s$ less than 90 degrees). A modified relationship would apply for forward-scatter (i.e. for $\theta_s$ greater than 90 degrees and less than 270 degrees). The most commonly used laser is a standard He-Ne type with radiation wavelength of 633 nm. The detector 30 can be a conventional photomultiplier (PMT) or a photodiode. The diameter of the laser radiation spot on the sample is typically 2 to 5 mm.

It is important to note that the range of the spatial frequency over which the scatterometer can measure is limited by the geometry of the apparatus and the wavelength of laser radiation used. For the arrangement illustrated in FIG. 1, the geometry restricts $\theta_s$ and $\theta_i$ to minimum values of approximately 1.5 degrees and 1.0 degrees, respectively. With x=633 nm, the range of f is approximately $0.015\mu^{-1}$ to $1.5\mu^{-1}$. This means that structure of spatial wavelength (lateral dimension) between approximately 70μ and 0.63μ can be detected using the arrangement illustrated in FIG. 1. By using laser light of shorter wavelength, structure of shorter spatial wavelength can be detected (e.g. for x=325 nm from a conventional He-Cd laser, structure with spatial wavelength as small as approximately 0.325μ can be detected).

A disadvantage of the prior art arrangement illustrated in FIG. 1 is that scattered light is not measured in a very efficient manner. The detector is moved in an arc, and at each position on the arc a measurement is made of the scattered light. This can be considered a sequential type of measurement; measurements made at the various positions on the arc are done in sequence, one after another. However, at all times the scattered light is passing through all positions. Typically, the number of measurement points is as large as 90 to 250. The time typically required to characterize the scattered light at one point on a sample ranges from minutes to more than an hour.

Figure 2:
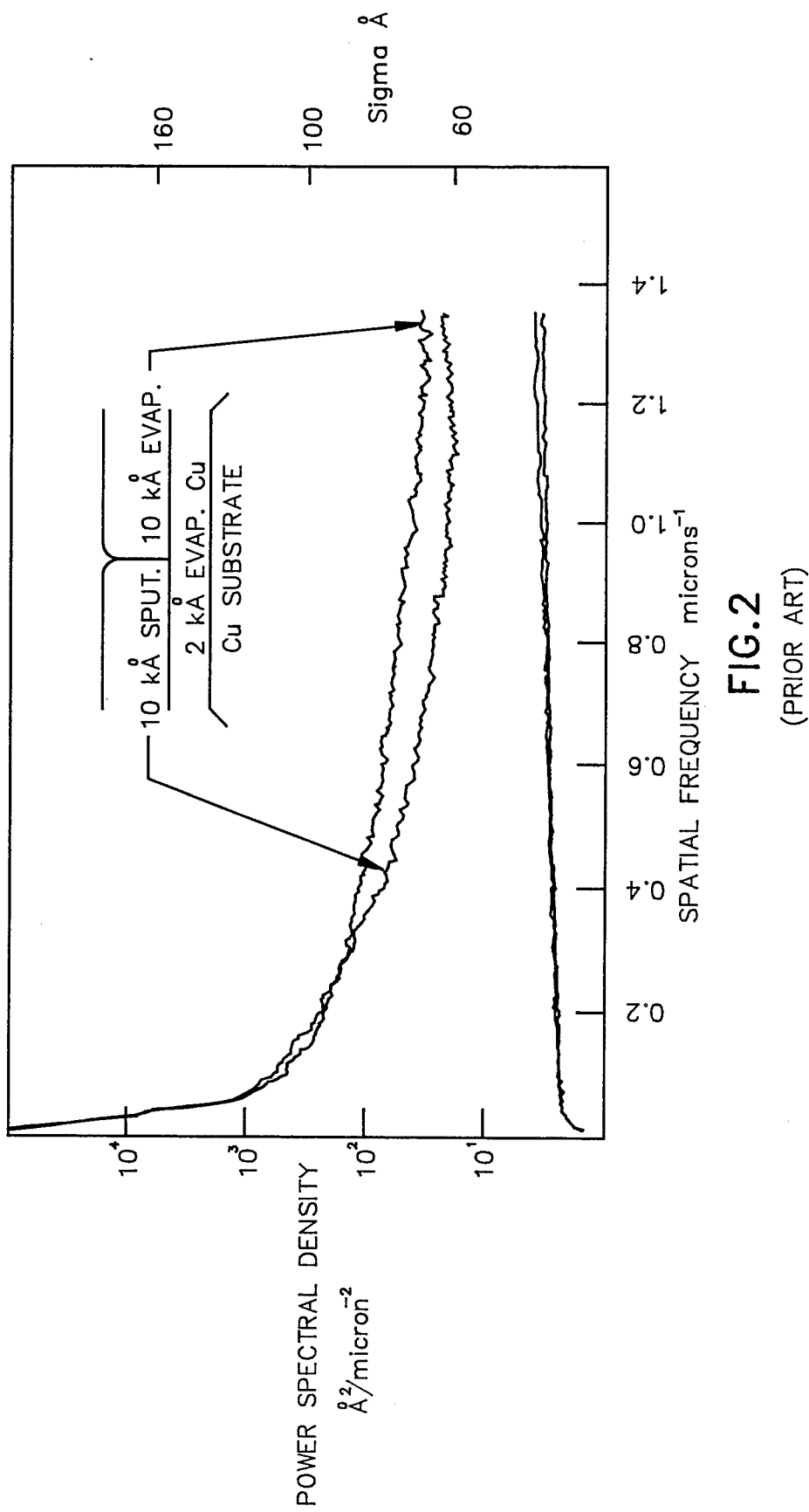
FIG. 2 is a plot of typical data collected from a scatterometer examination of two surfaces illustrating power spectral density (PSD) of the surface microstructure and r.m.s. microroughness of the surface as calculated from the PSD data.

Referring now to FIG. 2, there is shown a plot illustrating the data taken from an examination of two different samples. The left vertical scale of the plot is proportional to scattered intensity and is indicative of the amount of structure in some particular spatial frequency range of f to f +df. Thus, the plot represents the power spectral density of the microstructure on a surface. The same information can be plotted in a different manner which might be more suitable for specific applications (for example, scattered light in parts per million plotted versus scatter angle).

Figure 3:
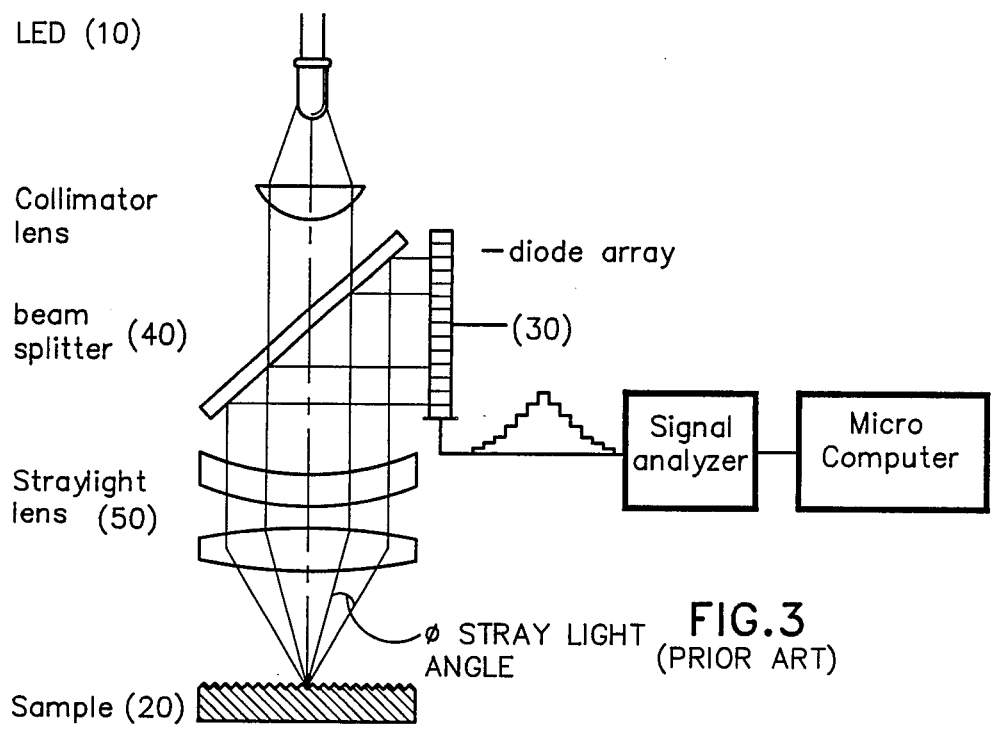
FIG. 3 is a diagrammatic representation of a multidetector scatterometer constructed in accordance with the prior art.

Referring now to FIG. 3, there is shown an improved prior art version of the scatterometer that employs a photodiode array of detectors 30 to monitor light scattered by a sample. Each diode of the array monitors the intensity of light scattered at a specific angle $\theta_s$. The advantage of this arrangement is that the measurement technique is efficient since measurements of scattered light at a number of different values of $\theta_s$ are performed simultaneously. This can be considered a parallel measurement scheme as opposed to a sequential arrangement. The arrangement of FIG. 3 is disadvantageous in several respects. The beam splitter 40 and the straylight lens 50 scatter some of the light passing through them. This, in turn, contributes to the overall level of light scattered by the entire scatterometer system independent of the sample being investigated, and this scattered light is detected by the photodiode array. This directly determines the minimum level of scattered light from a sample that can be detected. Therefore, the system is limited to measuring samples of r.m.s. microroughness of 5 nm or larger. This is much greater than the r.m.s. microroughness typical of samples encountered in optics and microelectronics fabrication, typically 0.5 nm to 2.0 nm r.m.s. microroughness. The straylight lens 50 also limits the range of microroughness spatial frequency, or lateral dimension, which can be examined. This is due to the straylight lens 50 being capable of collecting scattered light at angles $\theta_s$ of approximately 30 degrees or smaller. It is not feasible to have a lens with f-number smaller than 1. Because of this limitation, the lens diameter is smaller than the focal length of the lens. From FIG. 3, it can be seen that this requires the straylight angle $\theta_s$ to be less than approximately 30 degrees. From the equation set forth above, with $\theta_i=0$, this limits f to $\frac{1}{2}$x or smaller. The wavelength x of the typical light source for the arrangement represented in FIG. 3 is 820 nm. Thus, the system is limited to examining microstructure of spatial frequency approximately $0.6\mu^{-1}$ or less, or lateral dimension 1.6μ or larger. The wavelength used thus also limits the high spatial frequency (short lateral dimension measurement) capability of the system. Further, the prior art apparatus of FIG. 3 is useful only for examination of back-scattered light. There is no capability of examining light which is forward-scattered in a direction on the side of the sample opposite to that of the incident light. This would be useful when examining optical components, for example, which are transmitting light at the wavelength of examination. Lastly, the light source of the apparatus of FIG. 3 is a light emitting diode (LED) 10 with emission at 820 nm. In addition, the beam quality from a light emitting diode is not the high quality that is available from a laser. Specifically, this causes difficulty in distinguishing between the specularly reflected beam and light which is scattered at small scatter angle $\theta_s$. Because of this, the lower limit of $\theta_s$ must be larger than it would be if a laser were employed. This is especially important when considering that most samples back-scatter light in the near-specular direction (small $\theta_s$) as illustrated in FIG. 2. This represents a loss of information as well as a loss in scatterometer sensitivity. In addition, the scatterometer sensitivity suffers because of the long wavelength used due to the general dependence of total integrated scatter on wavelength. Total integrated scatter varies as $(1/x)^n$, where n is between 2 and 4.

Figure 4:
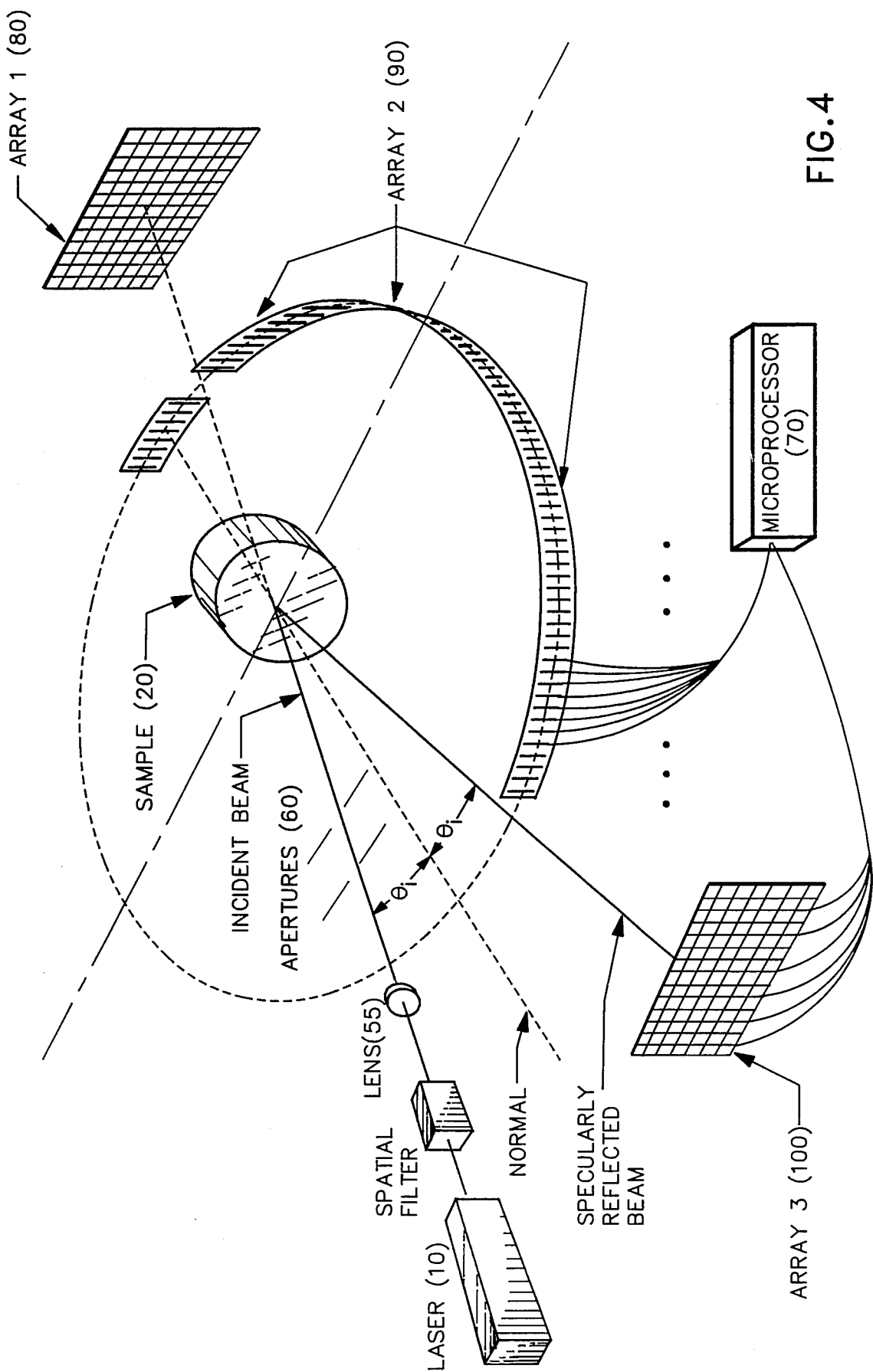
FIG. 4 is a diagram illustrating a multidetector scatterometer constructed in accordance with the present invention.

Referring now to FIG. 4, there is shown an optical scatterometer apparatus constructed in accordance with the present invention. The three arrays of detectors 80, 90, and 100 are employed for the following purposes. Array 80 is employed for detection of the incident laser beam without the sample in place. This would characterize the angular radiation characteristics of the incident beam and thus allow the quality of the optical system(i.e. the lens, spatial filter and possibly any other components in the incident beam) to be determined. In particular, an equivalent scatter characteristic of the optical system can be determined using this array. Array 90 is employed for detection of scattered light from the sample under test. Array 90 may extend from positions near the specularly reflected beam and in the plane of the incident and specularly reflected beams in an arc with center located on the sample, coincident with the incident laser radiation spot. This arc is the same arc as that of the detector 30 illustrated in FIG. 1. The array of detectors may extend for nearly 180 degrees or nearly 360 degrees of this arc. An additional array might be positioned in an arc located in a plane perpendicular to the plane of incidence and could be considered a portion of array 90. Array 100 is employed to monitor the specularly reflected beam. This would be used to determine proper alignment of the sample 20 to insure the sample is oriented with its normal in the proper direction. In addition, the readings from array 80 and array 100 may be used to determine a value for the sample reflectance. For example, taking the ratio of the detector readings would be one method of defining the sample reflectance.

The lens 55 of FIG. 4 is of sufficiently long focal length (approximately 50 cm) to allow use of multiple apertures 60 as illustrated. These apertures block stray light that could originate from the lens 55. There are no other elements to contribute to the scattered light level of the scatterometer system. This arrangement has been employed successfully to examine samples having less than 0.2 nm r.m.s. of microroughness. It should be noted that the focal length of lens 55 is such that the specularly reflected and transmitted (in the case of transmitting samples) laser beams are focussed at points located on the arc of array 90. However, these points do not lie on elements of array 90, and hence the specularly reflected and transmitted laser beams are incident on array 100 and array 80, respectively.

All three of the detector arrays 80, 90, and 100 may be either one-dimensional or two-dimensional arrays. Most practically, arrays 80 and 100 are two-dimensional and array 90 is one-dimensional.

Figure 5:
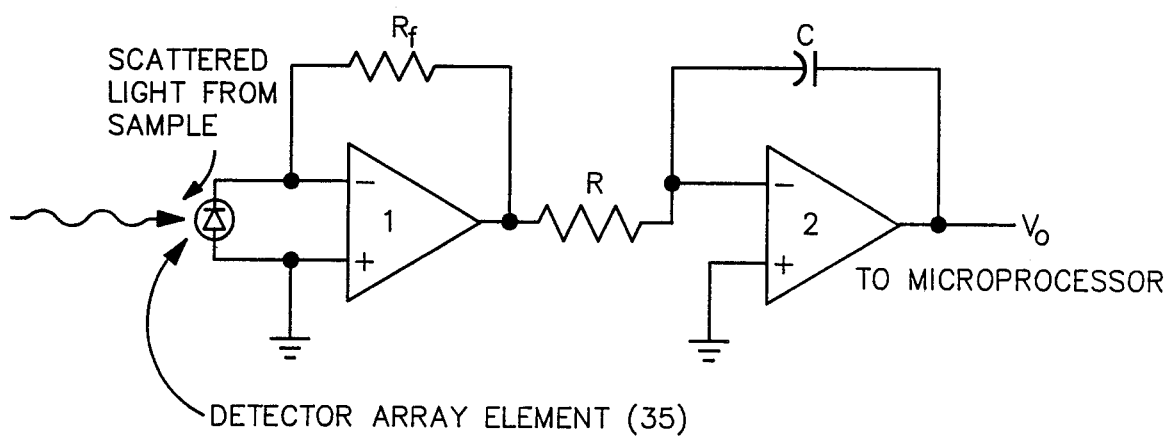
FIG. 5 is a schematic diagram of circuitry employed to process the signals received from each photodiode of detector array 90 of FIG. 4.

Each detector array element is interfaced to electronic processing circuitry. This can take the form of a conventional integrating circuit using standard operational amplifiers 1 and 2 shown in the circuit diagram of FIG. 5, for example. The silicon photodiode 35 in this case is connected in a photovoltaic detection arrangement as shown in FIG. 5. Signals from each electronic circuit would be monitored by a microprocessor 70 illustrated in FIG. 4. Microprocessor 70 may comprise for example a Hewlett-Packard Model 9816, an IBM PC, or one of a number of commercially available, less complex microprocessors. This microprocessor system would, for example, monitor the time required for each circuit output voltage $V_o$ to reach a specified predetermined value. This time would be inversely proportional to the intensity of scattered light incident on the various detector elements.

The detector array elements may comprise one of several detector types, such as silicon photodiodes, charge coupled devices (CCD), or pyroelectric devices. However, silicon photodiodes are most practical because of their large linear response range, low price, range of physical sizes easily available, and simple operation. The radius of the arc associated with array 90 is typically in the range of 5 to 50 cm. Given this arc dimension, a detector element size range of approximately 0.01 inches to as large as 0.50 inches is most practical. Note that this is not limiting size range, but only a practical example. Detector element shape may be circular, square or rectangular. Note that finer resolution in $\theta_s$ is required for making measurements of small $\theta_s$ (near the specular direction) as well as for $\theta_s$ near 180 degrees (near the directly transmitted beam) than is required for $\theta_s$ at intermediate values of $\theta_s$ between 20 degrees and 160 degrees, for example. Thus, array 90 could be arranged with small detector elements at the positions corresponding to small $\theta_s$ and $\theta_s$ near 180 degrees, and with detector elements increasing in size as $\theta_s$ approaches 90 degrees. This increasing element size is consistent with the need to detect smaller amounts of scattered light as $\theta_s$ approaches 90 degrees. This is consistent with data illustrated in FIG. 2, where it can be seen that scattered light (proportional to the PSD) decreases by nearly a factor of 10,000 for values of $\theta_s$ ranging from 1.5 degrees to 90 degrees.

The measurement technique is efficient in that measurements of scattered light at all the different values of $\theta_s$ (i.e. at each detector element of array 90) are performed simultaneously. This can be considered a parallel type of measurement. As such, the measurement time required to characterize a sample can be greatly reduced compared to the prior art arrangement illustrated in FIG. 1.

The detection arrangement of the present invention described in detail above and illustrated in FIG. 4 has certain distinct advantages over the prior art arrangements of FIGS. 1 and 3. First, the orientation of the detector array 90 of FIG. 4 eliminates the need for the beam splitter 4 and straylight lens 5 of the system illustrated in FIG. 3. Thus, the scatterometer system illustrated in FIG. 4 has an inherently lower level of system-scattered light (i.e. light which is scattered and detected, independently of the sample being investigated). This allows for examination of smoother samples which have lower levels of scatter. Samples of r.m.s. roughness less than 0.2 nm have been examined with the system illustrated in FIG. 4. Second, the arrangement of array 90 of FIG. 4, without the requirement that scattered light which is to be detected pass through the straylight lens 5 of FIG. 3, also provides for measurements over a wider range of microroughness spatial frequency or lateral dimension. This is because $\theta_s$ can extend to 90 degrees and larger instead of the 30 degrees or less for the prior art system illustrated in FIG. 3. This directly influences the range of spatial frequency which can be characterized by the equation set forth above. Third, the arrangement of array 90 of FIG. 4 provides for examination of reflecting as well as transmitting samples, thereby permitting examination of back-scatter and forward-scatter. This is important, for example, in examining glass optics. Fourth, the arrangement of array 90 of FIG. 4 can be used to characterize the light scattered from a sample in two orthogonal planes. This is useful to characterize the nonisotropic nature of the optical scatter, and thus the nonisotropic nature of the microstructure, such as would be found, for example, in diamond turned metal samples. In this case, an additional set of elements would be added to array 90, located in a plane perpendicular to the plane of incidence. Fifth, the light source in the system of FIG. 4 is a laser 10, which provides better beam quality than the LED of the prior art. Thus, scatter may be examined for smaller values of $\theta_s$ than is possible with the prior art systems. In addition, shorter wavelength light can be employed. This allows for higher ranges of microstructure spatial frequency to be examined and also increases the sensitivity of the scatterometer system. Further, two lasers may be conveniently employed to provide two wavelengths to examine a sample, one transmitted and one absorbed by the sample, as discussed above. Sixth, alignment of the optical system, including the sample, lens, spatial filter, and incident laser beam, can be easily automated using two dimensional arrays for array 80 and array 100. For example, the sample could be mounted in a holder that has angular (tip and tilt) adjustment provided by motor-driven screws such as motor driven micrometers. Once the sample is positioned in the holder, the signals from array 100 may be monitored to determine the location and direction of the specularly reflected beam. This is directly related to the angular orientation of the optical sample. Thus, by monitoring the signals from the two-dimensional array 100, the microprocessor system used to control the entire system can be used to actuate the motor-driven screws of the optical mount, thus providing automated angular adjustment of the sample under investigation. Sample reflectance may be calculated by using the signals from array 100 and array 80, as described above. Lastly, since there are no moving parts in the detector system, mechanical construction is greatly simplified. All three detector arrays remain fixed, once aligned.

I claim:

1. An optical scatterometer comprising:
   a material having optical and microstructure characteristics to be analyzed;
   laser means for transmitting an incident laser beam to irradiate a spot on the material;
   a first array of optical detectors positioned to detect the incident laser beam in the absence of said material for characterizing the optical characteristics of the incident laser beam;
   a second array of optical detectors positioned in a plane containing the incident laser beam and further positioned in a circular arc whose center coincides with the spot on the material irradiated by the incident laser beam, said second array of optical detectors being operative for detecting indications of both back-scattered and forward-scattered light resulting from irradiation of said spot on said material;
   a third array of optical detectors positioned to detect a specularly reflected beam of light from said material; and
   microprocessor means coupled to the first, second, and third arrays of optical detectors for processing electrical signals received therefrom to provide an indication to the user of the optical characteristics of the incident laser beam and of the optical and microstructure characteristics of said material.

2. An optical scatterometer system as in claim 1 wherein:
   a selected one or more of the optical detectors comprising said second array of optical detectors are positioned in a plane perpendicular to a plane containing said incident laser beam and said specularly reflected beam to detect indications of back-scattered and forward-scattered light in said plane perpendicular to said plane containing said incident laser beam and said specularly reflected beam.

3. An optical scatterometer system as in claim 1 wherein:
   said laser means comprises first laser means for transmitting a first incident laser beam having a first wavelength selected such that said first incident laser beam is substantially absorbed by said material; and
   said optical scatterometer system further comprises second laser means for transmitting a second incident laser beam having a second wavelength different from said first wavelength, said second wavelength being selected such that said second incident laser beam is transmitted by said material.

4. An optical scatterometer system comprising:
   a material sample having a film on a substrate, the optical and microstructure characteristics of which are to be analyzed;
   first laser means for transmitting a first incident laser beam to irradiate a spot on the film of said material sample, said first incident laser beam having a first wavelength selected such that said first incident laser beam is not transmitted by the film of said material sample;
   second laser means for transmitting a second incident laser beam to irradiate a spot on the substrate of said material sample, said second incident laser beam having a second wavelength selected such that said second incident laser beam is transmitted by the film of said material sample;
   a first array of optical detectors positioned to detect said first and second incident laser beams in the absence of said material sample for characterizing the optical characteristics of said first and second incident laser beams;
   a second array of optical detectors positioned in a plane containing said first and second incident laser beams and further positioned in a circular arc whose center coincides with said spot on the film of said material sample, said second array of optical detectors being operative for detecting indications of back-scattered and forward-scattered light resulting from irradiation of said spot on said film of said material sample and said spot on said substrate of said material sample;
   a third array of optical detectors positioned to detect a specularly reflected beam of light from said material sample; and
   microprocessor means coupled to the first, second, and third arrays of optical detectors for processing electrical signals received therefrom to provide an indication to the user of the optical characteristics of said first and second incident laser beams and of the optical and microstructure characteristics of said film and substrate of said material sample.

5. An optical scatterometer system comprising:
   a material having optical and microstructure characteristics to be analyzed;
   first laser means for transmitting a first incident laser beam to irradiate a spot on said material, said first incident laser beam having a first wavelength selected such that said first incident laser beam is substantially absorbed by said material;
   second laser means for transmitting a second incident laser beam to irradiate said spot on said material, said second incident laser beam having a second wavelength selected such that said second incident laser beam is transmitted by said material;
   one or more optical detectors positioned to detect indications of both back-scattered and forward-scattered light resulting from irradiation of said spot on said material; and
   microprocessor means coupled to said one or more optical detectors for processing electrical signals received therefrom to provide an indication to the user of the optical characteristics of said first and second incident laser beams and of the optical and microstructure characteristics of said material.

6. An optical scatterometer system as in claim 5 wherein said one or more optical detectors are positioned in a plane containing said first and second incident beams and are further positioned in a circular arc whose center coincides with said spot on said material.

7. An optical scatterometer system as in claim 5 wherein:
   said one or more optical detectors are positioned in a plane perpendicular to a plane containing said first and second incident laser beams to detect indications of back-scattered and forward-scattered light in said plane perpendicular to said plane containing said first and second incident laser beams.

8. An optical scatterometer system comprising:
   a material sample having a film on a substrate, the optical and microstructure characteristics of which are to be analyzed;

first laser means for transmitting a first incident laser beam to irradiate a spot on the film of said material sample, said first incident laser beam having a first wavelength selected such that said first incident laser beam is not transmitted by the film of said material sample;

second laser means for transmitting a second incident laser beam to irradiate a spot on the substrate of said material sample, said second incident laser beam having a second wavelength selected such that said second incident laser beam is transmitted by the film of said material sample;

one or more optical detectors positioned to detect indications of back-scattered and foward-scattered light resulting from irradiation of said spots on said film and substrate of said material sample; and microprocessor means coupled to said one or more optical detectors for processing electrical signals received therefrom to provide an indication to the user of the optical characteristics of said first and second incident laser beams and of the optical and microstructure characteristics of said film and substrate of said material sample.

9. An optical scatterometer system as in claim 8 wherein said one or more optical detectors are positioned in a plane containing said first and second incident laser beams and further positioned in a circular arc whose center coincides with said spot on said film of said material sample.

10. An optical scatterometer system as in claim 8 wherein:

said one or mroe optical detectors are positioned in a plane perpendicular to a plane containing said first and second incident laser beams to detect indications of back-scattered and forward-scattered light in said plane perpendicular to said plane containing said first and second incident laser beams.

* * * * *